(12) United States Patent
Benedetti (10) Patent No.: US 10,421,103 B2
(45) Date of Patent: Sep. 24, 2019

(54) ASSEMBLY FOR HANDLING FRUIT AND VEGETABLE PRODUCTS

(71) Applicant: UNITEC S.P.A., Lugo (IT)

(72) Inventor: Luca Benedetti, Ravenna (IT)

(73) Assignee: UNITEC S.P.A., Lugo (IT)

( * ) Notice: Subject to any disclaimer, the term of this patent is extended or adjusted under 35 U.S.C. 154(b) by 65 days.

(21) Appl. No.: 15/562,388

(22) PCT Filed: Mar. 23, 2016

(86) PCT No.: PCT/EP2016/056426
§ 371 (c)(1),
(2) Date: Sep. 27, 2017

(87) PCT Pub. No.: WO2016/156159
PCT Pub. Date: Oct. 6, 2016

(65) Prior Publication Data
US 2018/0281022 A1    Oct. 4, 2018

(30) Foreign Application Priority Data

Mar. 27, 2015 (IT) .............................. BO2015A0148

(51) Int. Cl.
*B07C 5/342* (2006.01)
*B65G 47/96* (2006.01)
(Continued)

(52) U.S. Cl.
CPC .............. *B07C 5/3422* (2013.01); *B07C 5/36* (2013.01); *B65G 47/962* (2013.01); *G01N 21/85* (2013.01);
(Continued)

(58) Field of Classification Search
CPC .. B07C 5/16; B07C 5/34; B07C 5/342; B07C 5/3422; B07C 5/36; B07C 5/361;
(Continued)

(56) References Cited

U.S. PATENT DOCUMENTS 4,106,628 A * 8/1978 Warkentin ................ B07C 5/18
177/145
4,726,898 A * 2/1988 Mills ......................... B07C 5/02
209/545
(Continued)

FOREIGN PATENT DOCUMENTS

EP 0556159 A2 8/1993
EP 1469301 A1 10/2004
(Continued)

OTHER PUBLICATIONS

International Search Report dated May 24, 2016 re: Application No. PCT/EP2016/05426; pp. 1-4; citing: WO 2007/000440 A1, GB 2 174 343 A, WO 93/15986 A1, EP 0 556 159 A2, EP 1 469 301 A1, US 5 626 236 A and US 2014/244026 A1.
(Continued)

*Primary Examiner* — Joseph C Rodriguez
(74) *Attorney, Agent, or Firm* — Cantor Colburn LLP (57) ABSTRACT

An assembly for handling fruit and vegetable products includes first containment units for fruit and vegetable products that can move along a first conveyance and/or control line. The assembly further includes second containment units for horticultural products that can move along a second conveyance and/or control line, which is laterally adjacent and proximate to the first line. The assembly includes a plurality of elements for transferring the horticultural products; such elements are distributed at least along a part of the first line and are selectively actuatable by an electronic management and control unit, for the transfer of each product from a first unit to a respective second unit in a portion chosen from a plurality of different portions of the first line, upon the occurrence of a predefined condition of mutual alignment between the horticultural product to be (Continued)

transferred, which is conveyed by the first unit, and a second unit.

8 Claims, 8 Drawing Sheets

(51) Int. Cl.
    *B07C 5/36*     (2006.01)
    *G01N 21/85*     (2006.01)
    *G01N 21/84*     (2006.01)

(52) U.S. Cl.
    CPC .................. *B07C 2501/009* (2013.01); *B65G 2201/0211* (2013.01); *G01N 2021/845* (2013.01); *G01N 2021/8466* (2013.01)

(58) Field of Classification Search
    CPC ............ B07C 5/362; B07C 2501/0081; B65G 47/962; B65G 2201/0211; G01N 21/85; G01N 2021/845; G01N 2021/8466
    See application file for complete search history.

(56) References Cited

U.S. PATENT DOCUMENTS

| | | | | |
|---|---|---|---|---|
| 5,230,394 A * | 7/1993 | Blanc | ...................... | B07C 5/18 177/145 |
| 5,335,767 A * | 8/1994 | Killer | ...................... | B07C 3/082 198/370.04 |
| 5,353,912 A * | 10/1994 | Killer | ...................... | B07C 3/082 198/370.04 |
| 5,626,236 A | 5/1997 | Hiebert | | |
| 6,179,129 B1 * | 1/2001 | Powell, Jr. | ............ | B07C 5/3422 177/145 |
| 6,374,983 B1 * | 4/2002 | Morigi | ................. | B65G 47/965 198/370.04 |
| 7,121,399 B2 * | 10/2006 | Mills | ....................... | B07C 5/363 198/438 |
| 7,131,904 B2 * | 11/2006 | Shefet | .................. | A22C 11/008 452/51 |
| 8,061,501 B2 * | 11/2011 | Benedetti | ............. | B65G 47/244 198/385 |
| 9,004,287 B2 * | 4/2015 | Liedl | ......................... | B07C 5/16 209/541 |
| 9,886,752 B2 * | 2/2018 | Taylor | .................... | G01G 17/00 |
| 2008/0185267 A1 * | 8/2008 | Benedetti | ............. | B65G 47/965 198/705 |
| 2014/0244026 A1 | 8/2014 | Neiser | | |

FOREIGN PATENT DOCUMENTS

| | | |
|---|---|---|
| GB | 2174353 A | 11/1986 |
| WO | 9315986 A1 | 8/1993 |
| WO | 2007000440 A1 | 1/2007 |

OTHER PUBLICATIONS

Written Opinion dated May 24, 2016 re: Application No. PCT/EP2016/05426; pp. 1-11; citing: WO 2007/000440 A1, GB 2 174 343 A, WO 93/15986 A1, EP 0 556 159 A2, EP 1 469 301 A1, US 5 626 236 A and US 2014/244026 A1.

* cited by examiner

ASSEMBLY FOR HANDLING FRUIT AND VEGETABLE PRODUCTS

TECHNICAL FIELD

The present disclosure relates to an assembly for handling fruit and vegetable products.

BACKGROUND

Companies that develop automated systems for handling and checking large quantities of fruit and vegetable products often find themselves faced with problems that are not easy to resolve.

In fact, even when the system is intended for use with a single, specific type of product (a fruit for example), it is usually fed upstream with great quantities of products that arrive at the factory directly from the harvest fields, and which therefore exhibit enormous variability in size and weight.

The need is therefore felt to provide automated lines that are capable of distributing products of different size categories to a plurality of receiving stations, in that often fruits (or other fruit and vegetable products) of greater size (or greater weight) cannot be sent for subsequent processing, or to end consumers, together with the smaller fruits.

Moreover it seems evident that in an industrial context, and therefore in systems and lines that are at least partially automated, precisely this enormous variability requires maximum care on the part of the companies that make them, in that the lines and the handling elements must be sufficiently versatile to be able to cater for the different formats with which pears, apples, strawberries, cherries, etc., are presented.

To such heterogeneity we must also add the great variety of defects that fruits can exhibit, and which the system must be capable of intercepting, in order to send to the downstream stations only those products that fall within the preset quality parameters (which are moreover increasingly stringent), and diverting for reprocessing, or simply discarding, those fruits that are rotten or bruised, are showing initial signs of early decay, or that exhibit other defects.

In such context, one of the fruits that pose the most difficulties is certainly the pear: in order to be able to identify the defects and at the same time check its color and weight (and therefore its size category), systems are known that involve the use of video cameras for checking which are arranged along fruit handling lines and are capable of identifying the defects.

Such systems usually have two handling lines, side by side, in that after a first video camera has conducted a first check on the pear being conveyed on the first line, in order to detect its shape, size, color, any surface and pulp flaws, etc., the pear is tipped over and transferred to the second line, where a second video camera performs a second check on the other side of the pear, to complete the analysis.

However, the peculiar shape of the pear makes it substantially impossible to check the exact arrangement with which the pear is deposited and conveyed on the first line and, especially, at what point of the respective containment unit the pear is consequently laid and conveyed along the second line.

This complicates the second check and, especially, it makes it necessary to have a third line or station for carrying out the weighing, in that for such activity it is necessary to be able to count on a certain position (usually corresponding to the center of the containment unit), in order to obtain an exact measurement by the load cells and/or of the other sensors that are usually used.

The aim of the present disclosure is to solve the above mentioned problems, by providing a handling assembly that makes it possible to transfer fruit and vegetable products between two handling lines, while at the same time being able to control their positioning, at least on the downstream line.

Within this aim, the disclosure provides an assembly for handling fruit and vegetable products, which makes it possible to check the color, the size category and/or the presence of flaws thereon, and at the same time make it possible to weigh them.

The disclosure further provides a handling assembly that ensures a high reliability of operation.

The disclosure also provides a handling assembly that can be easily implemented using elements and materials that are readily available on the market.

The disclosure provides a handling assembly that is low cost and safely applied.

These advantages and others are achieved by providing an assembly for handling fruit and vegetable products, which comprises first containment units for fruit and vegetable products that can move along a first conveyance and/or control line and second containment units for horticultural products that can move along a second conveyance and/or control line, which is laterally adjacent and proximate to said first line, characterized in that it comprises a plurality of means for transferring the horticultural products, said means being distributed at least along a part of said first line and being selectively actuatable by an electronic management and control unit, for the transfer of each product from a said first unit to a respective said second unit in a portion chosen from a plurality of different portions of said first line, upon the occurrence of a predefined condition of mutual alignment between the horticultural product to be transferred, which is conveyed by said first unit, and a said second unit.

BRIEF DESCRIPTION OF THE DRAWINGS

Further characteristics and advantages of the disclosure will become better apparent from the description of a preferred, but not exclusive, embodiment of the handling assembly according to the disclosure, which is illustrated by way of non-limiting example in the accompanying drawings wherein.

DETAILED DESCRIPTION OF THE DRAWINGS

With reference to the figures, the reference numeral 1 generally designates an assembly for handling horticultural products such as fruit and vegetable products, which first of all comprises first containment units 2*a* of fruit and vegetable products A, which can move along a first conveyance and/or control line 3*a*.

It should be noted from this point onward that in the preferred application of the disclosure, to which reference will often be made in the present discussion, the fruit and vegetable products A are pears, whose peculiar shape poses many problems for the companies that make conventional conveyance and checking systems (problems that, as will be seen, will be solved by the assembly 1 according to the disclosure).

In any case it should be emphasized that the possibility is not ruled out of using the assembly 1 according to the disclosure for handling, conveying and/or checking other fruits or fruit and vegetable products A in general.

Furthermore, the assembly 1 comprises second containment units 2*b* of the fruit and vegetable products A, which can move along a second conveyance and/or control line 3*b*, which is conveniently arranged laterally adjacent and proximate to the first line 3*a*.

As in the accompanying figures, the lines 3*a*, 3*b* can define for the respective unit 2*a*, 2*b* straight paths that are entirely arranged side-by-side, but assemblies 1 can also be provided in which the lines 3*a*, 3*b*, although being side-by-side and mutually proximate in at least one segment thereof, are curvilinear or mixtilinear, according to the specific logistical requirements that may for example apply inside the building for which the assembly 1 is intended.

According to the disclosure, the assembly 1 comprises a plurality of means for transferring the fruit and vegetable products A, which are distributed and act at least along one part of the first line 3*a*.

Such means can therefore be selectively actuated by an electronic management and control unit, so as to cause the transfer of each product A from a first unit 2*a* to a respective second unit 2*b* in a portion chosen from a plurality of different portions of the first line 3*a*. More precisely, and thanks to the presence of a plurality of means that act along the first line 3*a*, the transfer can be effectively commanded upon the occurrence of a predefined condition of mutual alignment between the fruit and vegetable product A to be transferred, which is conveyed up until that moment by the first unit 2*a*, and a second unit 2*b*.

It should be noted in fact that the impossibility of establishing in advance the position assumed by each pear in the respective first containment unit 2*a* makes it impossible to identify (at the design stage) a point of the first line 3*a* at which, for all pears, a predefined condition of mutual alignment occurs, and it is even less possible to ensure to this end that both the lines 3*a*, 3*b* move at the same speed.

By contrast, such condition for mutual alignment is in fact made necessary by the need to control the positioning of the fruit and vegetable products A at least in the second units 2*b*, in order to ensure that each pear is located at the same point of each second unit 2*b*.

Thanks to the means for transfer therefore, the electronic unit can choose in each instance, for each pear, the best portion of the first line 3*a* at which to perform the transfer, in this way being able to control the positioning thereof along the second line 3*b*, and already achieving the set aim.

In fact, by conveniently choosing the condition for mutual alignment, it is for example possible to ensure that each pear is transferred to the respective second containment unit 2*b* at a specific point (of a specific part) of the latter, so achieving the desired control of the positioning.

It should be noted that the electronic unit can be freely chosen: it can in fact be an electronic controller, a (micro) processor, a CPU, a PC, a computer etc.

Precisely with reference to the preferred (but not exclusive) embodiment, each second containment unit 2*b* is associated with a respective device for weighing the fruit and vegetable product A being conveyed.

Any type of device for weighing can be used, and for example each second unit 2*b* can be provided with a respective load cell.

It should be noted that weighing devices of the type indicated above necessitate an exact positioning of the product A with respect to the second unit 2*b* that accommodates it, in order to be able to operate correctly: in such context, it is therefore evident that the assembly 1 ensures an optimal weighing, thanks to the possibility of choosing the moment in which to perform the transfer toward the second containment unit 2*b*.

Figure 1:
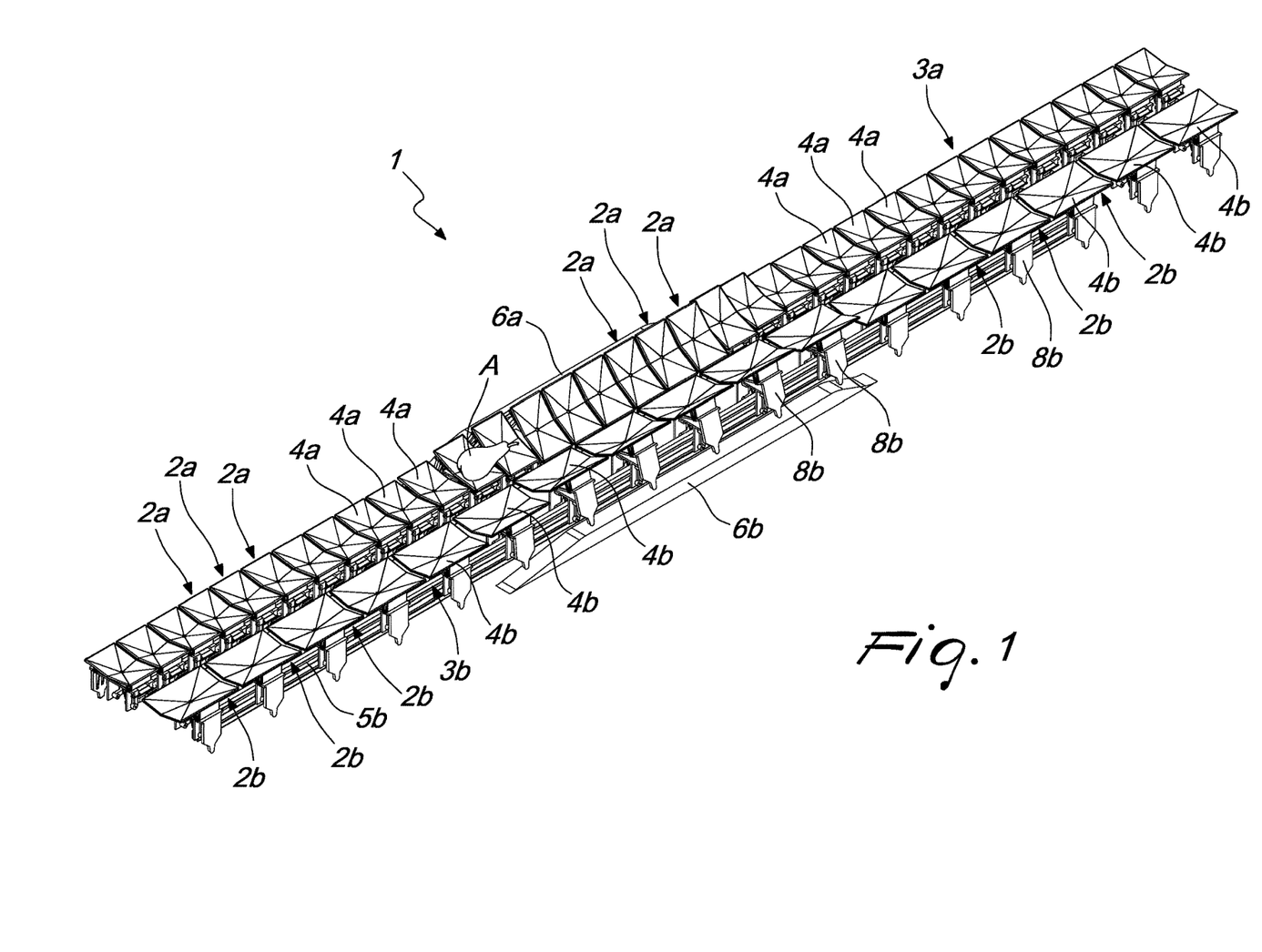
FIG. 1 is a perspective view from the right-hand side of a handling assembly according to the disclosure.
Figure 2:
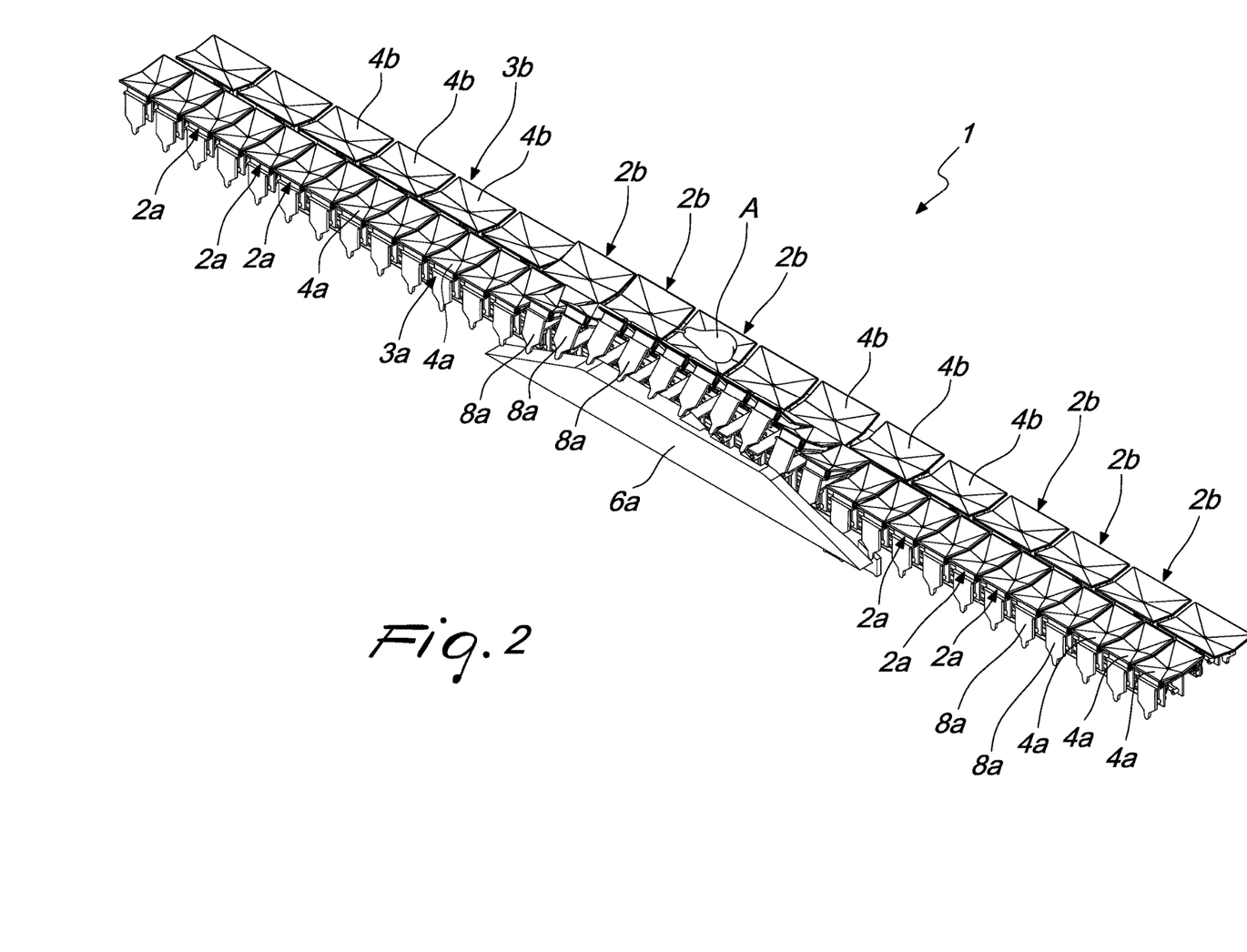
FIG. 2 is a perspective view from the left-hand side of the handling assembly in FIG. 1.

With further reference to the preferred embodiment of the disclosure, the assembly 1 comprises an electronic control apparatus, which in turn is provided with a first video camera that faces the first line 3*a* and is capable of checking the color, the size and/or the presence of surface and pulp flaws of various types on the fruit and vegetable products A, while these are supported and conveyed by the first units 2*a* in a first arrangement. It should be noted that such first arrangement (in which a pear is for example shown in FIG. 1) usually corresponds to the position with which each product A has been deposited on the respective first containment unit 2*a*, in the initial segment of the first line 3*a*. In such first arrangement, each product A is therefore conveyed along the first line 3*a* and its surface portion directed upwardly can thus be checked by the first video camera, above the first line 3*a*.

Figure 3:
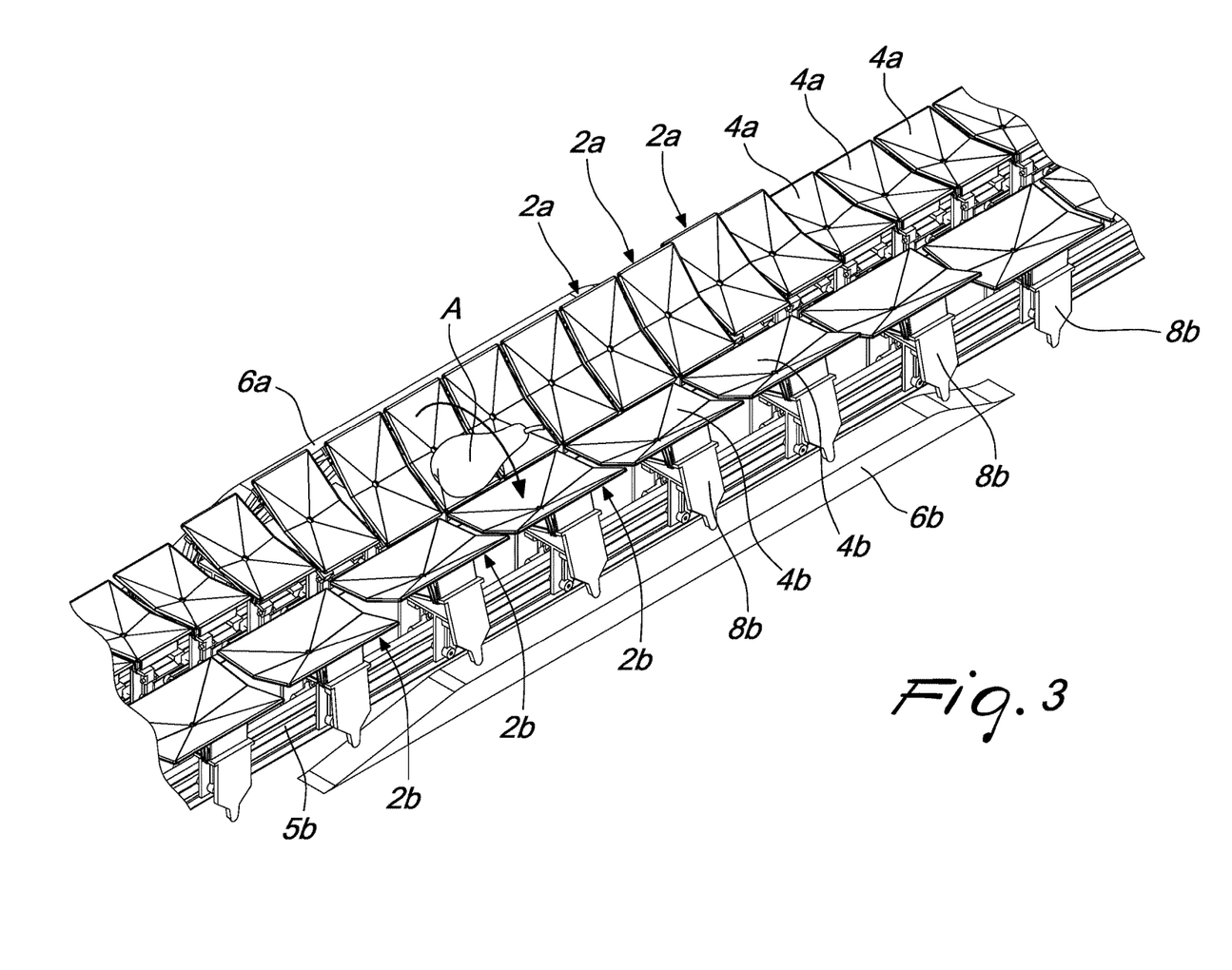
FIG. 3 is a first detail of FIG. 1.

Furthermore, the control apparatus 2*b* is provided with a second video camera that faces the second line 3*b*, so that it can also check the color, the size and/or the presence of surface and pulp flaws of various types on the fruit and vegetable products A, while they are supported and conveyed by the second units 2*b* in a second arrangement (in which a pear is for example shown in FIG. 3), obtained automatically as a consequence of the transfer of the products A from the first line 3*a* to the second line 3*b*.

More precisely, the transfer causes the partial rotation of each pear, which thus assumes a second arrangement and directs a different surface portion upwardly, which can therefore in turn be checked by the second video camera (above the second line 3*b*), thus completing the check of the color, the size category and/or the presence of any flaws (and of the shape and size) for each fruit and vegetable product A.

It should be noted therefore that in the preferred embodiment the assembly 1 is effectively capable of weighing each pear (or other fruit and vegetable product A) and/or of checking for the presence therein of surface flaws (over the entire surface) and pulp flaws and/or, more simply, of measuring its size.

It should be noted again that the possibility is still not ruled out of adopting the innovative concepts illustrated herein for different handling assemblies 1.

In the embodiment illustrated in the accompanying figures for the purposes of non-limiting example, each first unit 2*a* is constituted substantially by a first tray 4*a*, which can move along a first guiding track 5*a* which substantially defines the first line 3*a*. Furthermore, each first tray 4*a* is rotatable about to a first main axis, substantially parallel to the first track 5*a*: the previously-mentioned means therefore comprise elements for actuating the rotation of respective first trays 4a about the first main axis. As can be seen for example from FIG. 3, the rotation thus produces the partial tipping of the respective first tray 4a, and this causes the consequent transfer of the corresponding fruit and vegetable product A (which is in turn overturned) toward the respective second unit 2b.

It should be noted further that as a consequence of the tipping, the fruit and vegetable product A automatically passes from the first arrangement to the second arrangement (in order to allow the complete checking for any flaws present, as we have already seen).

Conveniently, in order to be able to perform the transfer in the predefined condition of mutual alignment, the control apparatus comprises an electronic viewer (optionally coinciding or integrated with the first video camera) associated with the electronic unit and arranged along the first line 3a. The viewer in fact is capable of acquiring, according to conventional methods, information about the position assumed by each fruit and vegetable product A in the respective first unit 2a. In turn, the electronic unit will be provided with an algorithm for calculating the portion (of the point) of the first line 3a corresponding to the occurrence of the predefined condition of mutual alignment, as a function of the shape and of the speed of the first unit 2a and of the second unit 2b, and of the position detected by the viewer.

Therefore, whatever the position assumed by the pear in the respective first tray 4a, the electronic unit is capable of calculating and identifying the moment at which the predefined condition of mutual alignment arises, in order to command, right at that moment, the transfer of the pear to the second line 3b, thus obtaining an exact and repeatable positioning on the second units 2b.

It should be noted that the electronic management and control unit can be freely programmed to choose any predefined condition of mutual alignment. In the preferred embodiment in any case, such predefined condition corresponds to the alignment of the fruit and vegetable product A to be transferred, which is conveyed by the respective first unit 2a, with the central portion of a respective second unit 2b, so that the fruit and vegetable product A is arranged exactly in such central position. As we have already seen in fact, in this manner it is possible to obtain the correct weighing of each pear, in that the device designed for this purpose operates best when the pear is exactly positioned in the center of the second unit 2b.

In the embodiment illustrated in the accompanying figures, and in a manner similar to what was observed for the first units 2a, each second containment unit 2b is constituted substantially by a second tray 4b, which can move along a second guiding track 5b which substantially defines the second line 3b and has a shape and dimensions that are optionally different from those of the first tray 4a. It should be noted in fact that in the solution to shown, each second tray 4b, although being rectangular in plan like the first tray 4a, with respect to the latter is appreciably larger (and is oriented with the long sides parallel to the second track 5b). This in fact makes it possible to obtain a better positioning of the pears in the second units 2b, and therefore a more exact weighing.

Furthermore, and in further analogy with the first units 2a, each second tray 4b can also rotate, about a second main axis which is substantially parallel to the first main axis and to the second track 5b. This therefore makes it possible to obtain the partial tipping of the second trays 4b in the opposite direction to that of the partial tipping of the first trays 4a, at least during the transfer of the respective fruit and vegetable product A.

In this manner in fact, when the pear is transferred to the second unit 2b, the partial tipping thereof reduces (guards against) the danger that the transfer occurs without the necessary gentleness and/or that an excessive thrust could make the pear fall from the second line 3b, overshooting the second tray 4b.

In particular, in order to perform the tipping of the first trays 4a (and the transfer of the pears) at a chosen portion of the first line 3a, the means for transferring comprise at least one first guiding plate 6a, which faces in a parallel arrangement and is proximate to the first line 3a on the opposite side with respect to the second line 3b.

Figure 7:
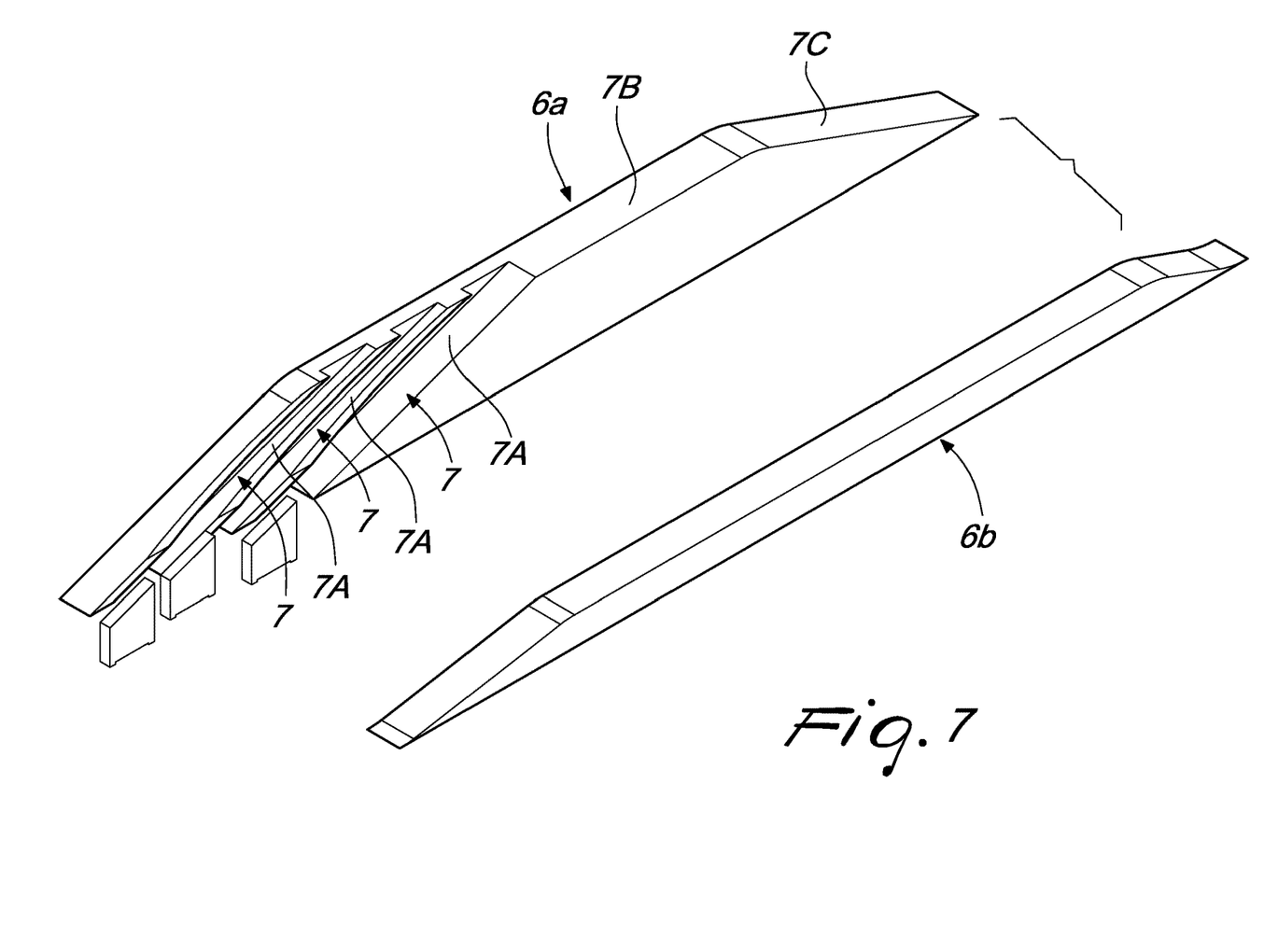
FIG. 7 is a perspective view from the right-hand side of further components of the assembly in FIG. 1.
Figure 8:
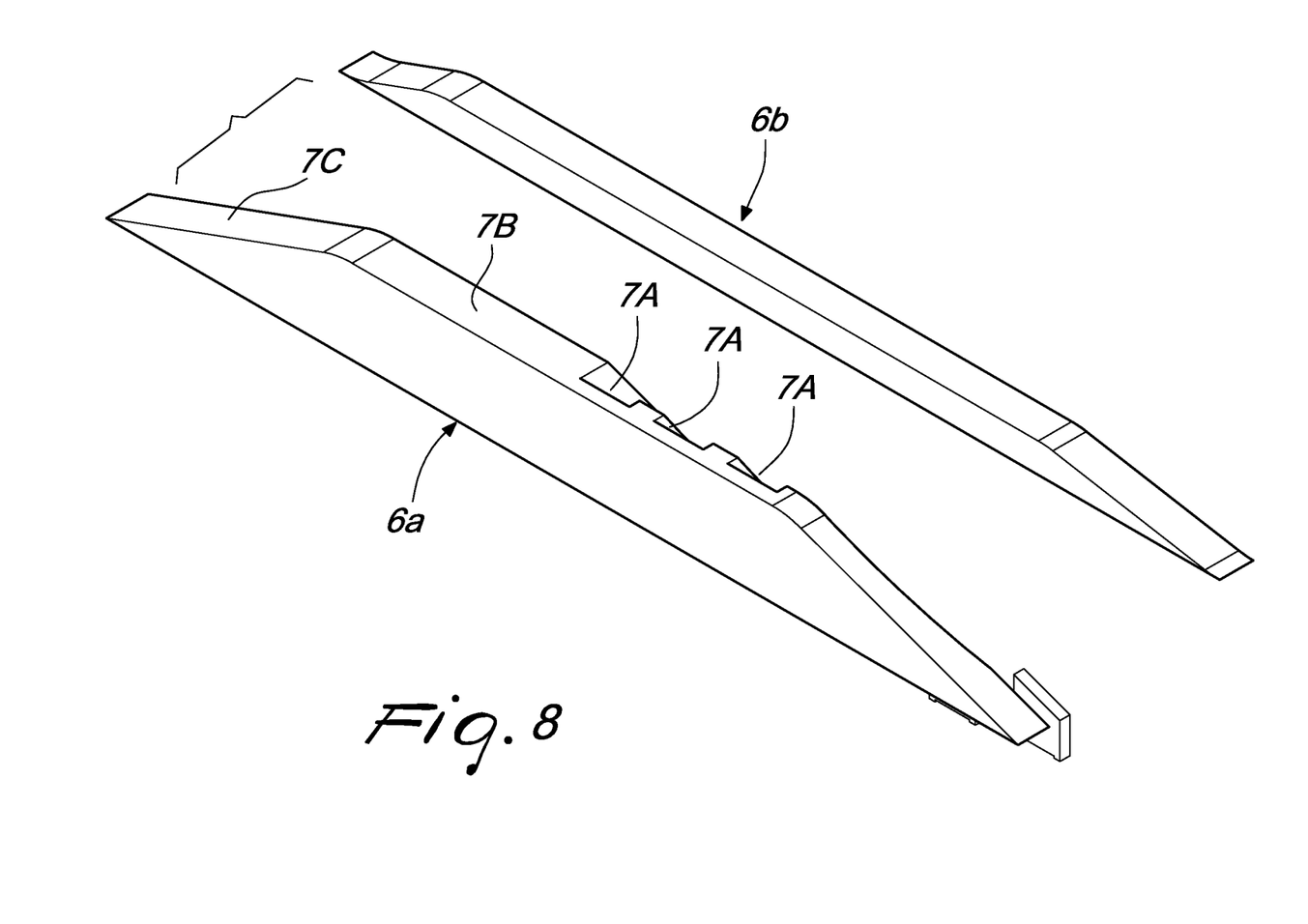
FIG. 8 is a perspective view from the left-hand side of the components in FIG. 6.

As can be seen clearly for example from FIG. 7, at least along the lateral wall of the first plate 6a that directly faces the first line 3a, there is a plurality of inclined lanes 7: following the actuation of the corresponding actuation element, a first shank 8a with which each first tray 4a is provided can selectively engage in each lane 7, so as to cause the rotation of the corresponding first tray 4a as a consequence of the sliding of the first shank 8a in the lane 7.

So, effectively, each lane 7 behaves like a cam that imposes a specific movement on the first shank 8a with which it engages, and therefore causes the rotation of the respective first tray 4a, which is integral with the first shank 8a.

More specifically, each actuation element (not shown for the sake of simplicity in the accompanying figures) comprises at least one actuator (which can be conventional), which is integral with the respective first unit 2a and which usually faces the first shank 8a. Each actuator can be selectively actuated by the electronic unit (upon the occurrence of the predefined condition of mutual alignment or in the moments immediately preceding it) in order to force the engagement of the first shank 8a in a corresponding lane 7, thus obtaining the desired rotation of the first tray 4a which is carrying the pear to be transferred to the second line 3b.

In the embodiment proposed for the purposes of non-limiting example in the accompanying figures, and with specific reference to FIG. 7, following the engagement the first shank 8a follows a first inclined corridor 7A, then proceeds along the straight back 7B of the first plate 6a, and finally descends along a ramp 7C. Such progression obviously causes a corresponding rotation of the respective first tray 4a, to which the first shank 8a is anchored.

Advantageously, the handling assembly 1 according to the disclosure comprises a second guiding plate 6b, which in turn faces in a parallel arrangement and is proximate to the second line 3b on the opposite side with respect to the first line 3a. Differently from what was seen for the first plate 6a (which can intercept the first shanks 8a only following the activation of the actuation element), the second plate 6b is arranged along the path of second shanks 8b of each second tray 4b.

As can be seen from the accompanying figures, such choice causes the rotation of each second tray 4b (when they arrive at the second plate 6b) in that the respective second shank 8b is forced to slide on a contoured run defined by the top of the second plate 6b.

The second plate 6b therefore also behaves like a cam, but it imposes the same travel and the same partial tipping (at the same portion of the second line 3b) on all the second trays 4b.

As can be seen from the accompanying figures, by conveniently choosing the length of the track (equal to the full extension of the first plate 6a, affected by the various lanes 7), the second trays 4b are kept partially inclined for the entire segment of the second line 3b in which they can potentially receive a pear.

While not ruling out the provision of assemblies 1 in which the second plate 6b has lanes 7 similar to those described for the first plate 6a, for selectively engaging with the second shanks 8b, the choice to impose the same tipping on all the second trays 4b simplifies the structure (and the cost) of the assembly 1, while still ensuring in any case the functionality described up to now.

It should moreover be noted that the possibility is not ruled out of offering assemblies 1 on the market, and wherein the second units 2b are not subjected to any rotation (and wherein, for example, the risk of falling of the pears is more simply guarded against by side walls suitably arranged along the outer side of each second tray 4b).

Figure 4:
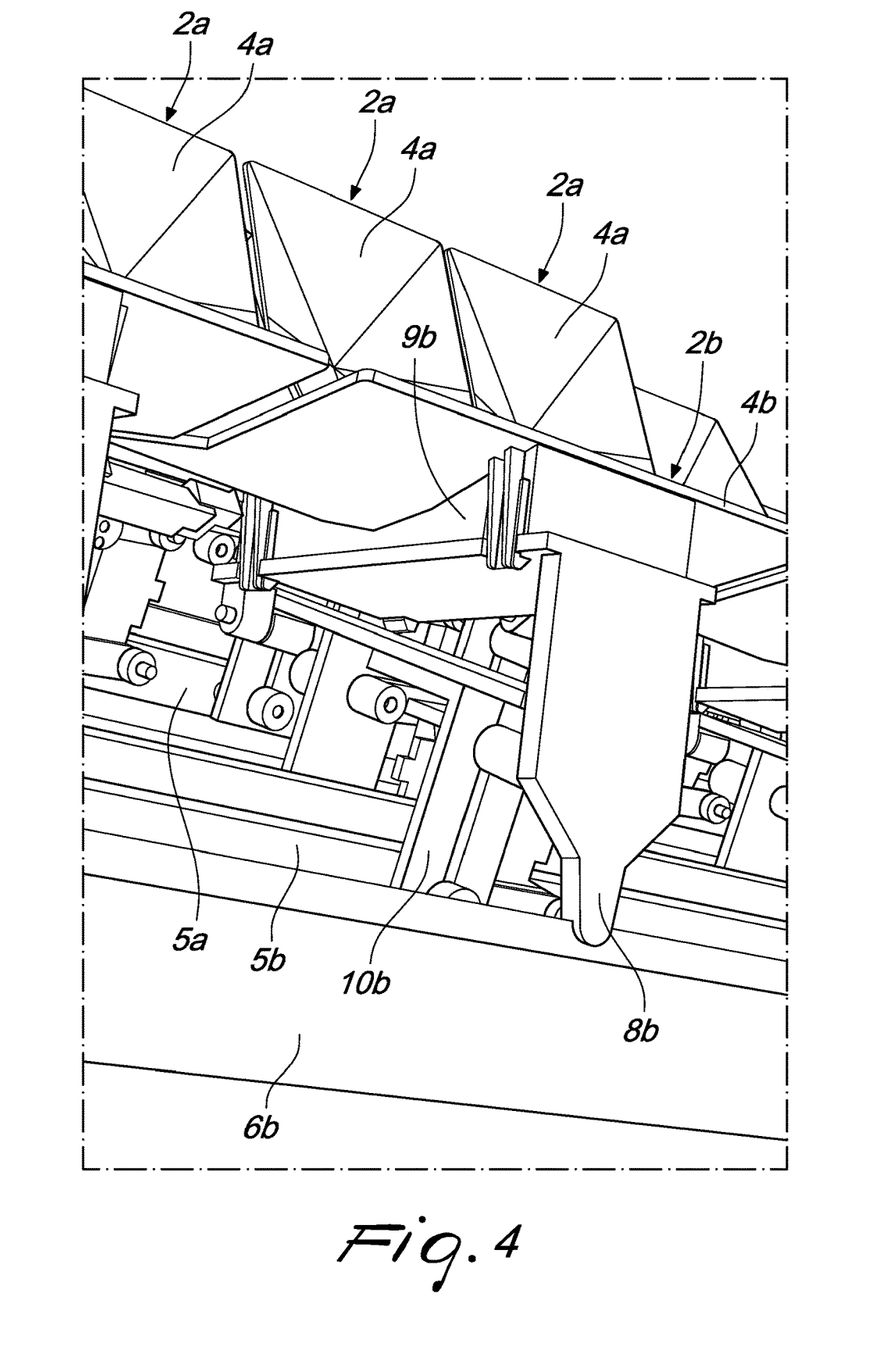
FIG. 4 is an enlarged second detail of FIG. 1.
Figure 5:
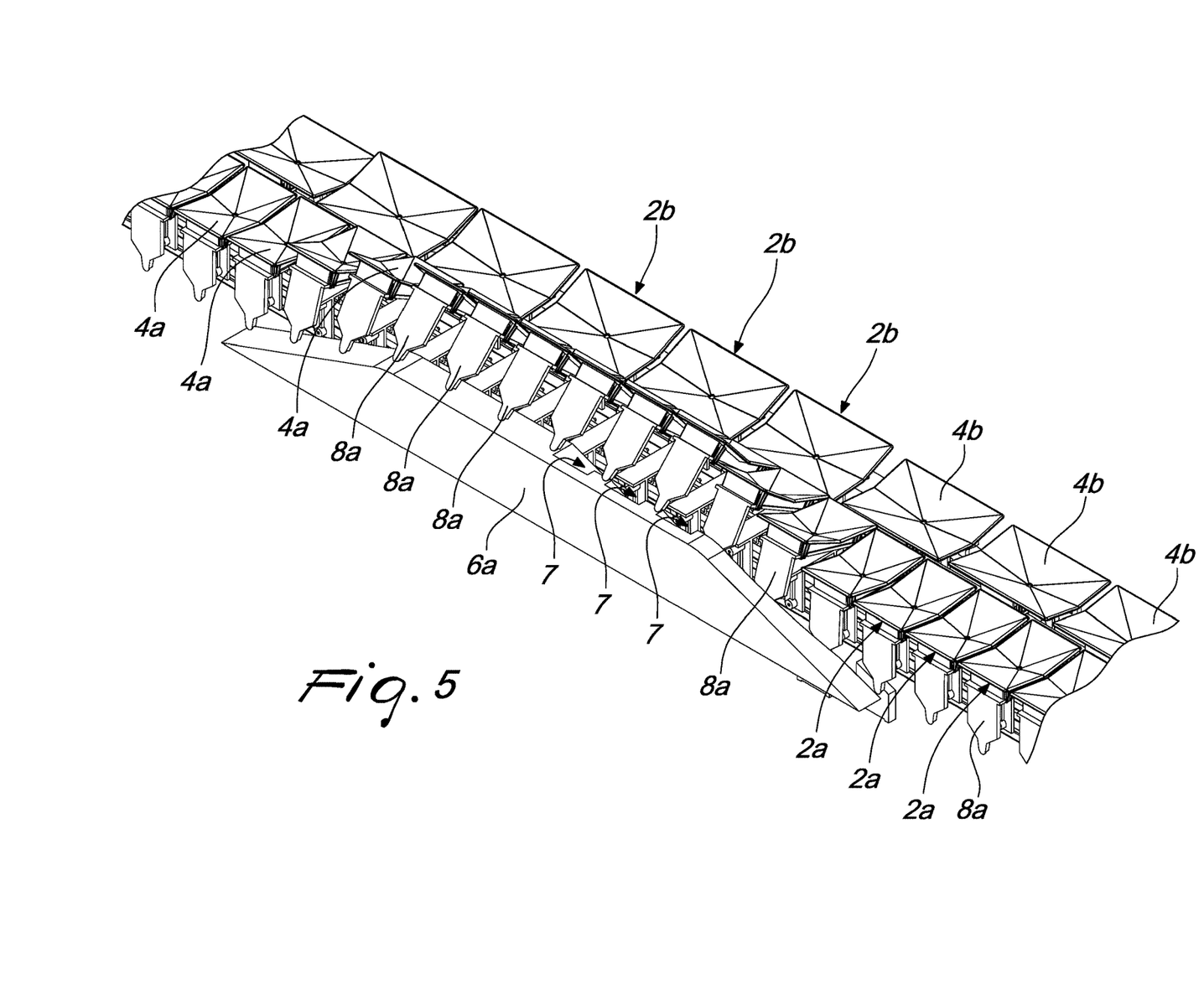
FIG. 5 is an enlarged detail of FIG. 2.
Figure 6:
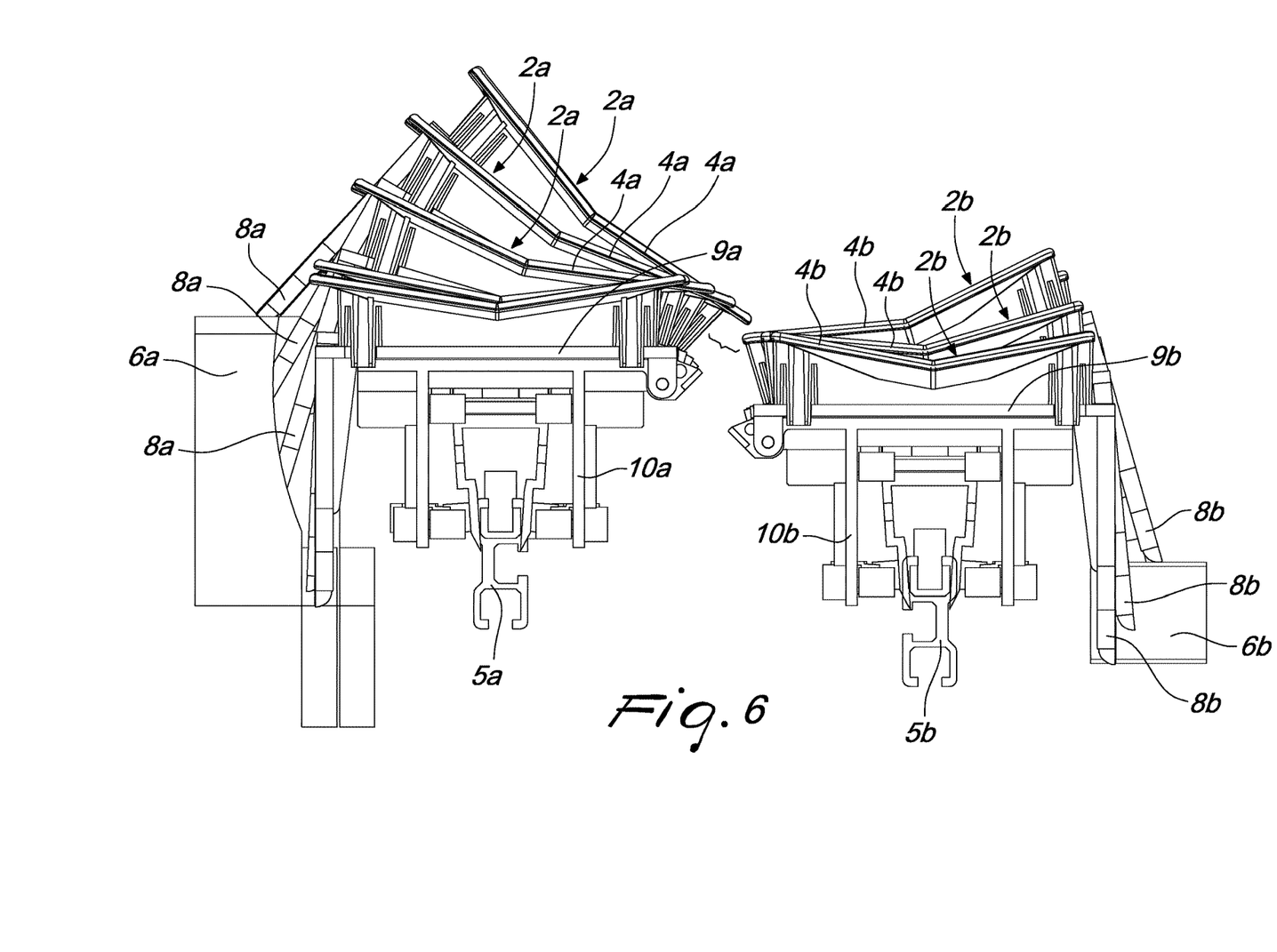
FIG. 6 is a front elevation view of some components of the assembly in FIG. 1.

Advantageously, as can be seen in particular from FIGS. 4 and 7, each tray 4a, 4b (therefore for each line 3a, 3b) is rigidly supported by a support 9a, 9b, which is pivoted, about the respective main axis, to a slider 10a, 10b which can slide along the corresponding track 5a, 5b.

Each shank 8a, 8b therefore extends from the corresponding support 9a, 9b, on the opposite side with respect to the corresponding tray 4a, 4b.

Therefore for the second line 3b, when the second unit 2b arrives at the second plate 6b, the respective second shank 8b rises along the top of the latter and this causes the rotation of the support 9b and of the second tray 4b.

Conversely, in the first line 3a the first shank 8a (or at least one of its ends) follows one of the lanes 7 only when the actuator pushes it against that lane: by providing an appropriate number of lanes 7 it is thus possible to define a plurality of portions (points of the first line 3a) at which to make the partial tipping of each first tray 4a occur.

Operation of the handling assembly according to the disclosure is the following.

Each pear (or other fruit and vegetable product A) is loaded onto a first unit 2a of the first line 3a in a first arrangement, which is random and not predictable in advance, even in light of the irregular shape of such fruits.

The pears are thus initially conveyed along the first line 3a, where a first video camera can detect its color, shape and size and/or check for the presence of surface flaws on the exposed portion or flaws in the pulp.

Furthermore, in this step an electronic viewer associated with the electronic unit acquires information about the position assumed by each fruit and vegetable product A in the respective first unit 2a: preferably, such information relates to both the orientation with which the product A is placed on the first tray 4a (the first arrangement mentioned above), and the point of the first tray 4a at which the product A is located (with respect to fixed references, such as for example its perimeter or its center). This therefore enables the electronic unit to calculate the portion of the first line 3a where to make the transfer occur (this is chosen to correspond to the occurrence of the predefined condition of mutual alignment).

In order to carry out the transfer, the electronic unit actuates the actuator associated with the first unit 2a which is carrying the product A to be transferred; the actuator in fact pushes the first shank 8a of the corresponding first tray 4a toward the first plate 6a, engaging the first shank 8a with a chosen one of the several lanes 7. Thus, a specific travel along the lane 7 is imposed on the first shank 8a and, as a consequence, the first tray 4a rotates, tipping over partially and transferring the pear to the side, where it is received by a second containment unit 2b.

Thanks to the calculation performed by the electronic unit, it is possible to position every pear in the center of the respective second tray 4b, so as to enable an easy weighing operation.

Furthermore, with the tipping the products A change their configuration (the orientation with which they are placed on the second unit 2b), and therefore they are conveyed along the second line 3b in a second arrangement, in which they show a different surface portion (substantially opposite and complementary to the previous one) to a second video camera, thus enabling the completion of the check of flaws, color and size category.

It should be noted however that if the first video camera detects serious flaws on a pear, the electronic unit can omit to command the transfer, so allowing the fruit and vegetable product A to continue on its way until the end of the first line 3a, where it can be allowed to fall into a container of discarded material. Or, by way of using further elements of the type of guiding plates 6a, 6b, arranged upstream and/or downstream of the lines 3a, 3b, the assembly 1 can be given the capability to unload the products A at the sides of the lines 3a, 3b, in order to discard them upon the detection of serious flaws and/or route them to conveniently provided reprocessing stations.

Differently from what occurs with conventional systems, it has therefore been fully shown that the assembly 1 according to the disclosure makes it possible to determine with precision the point of the second containment unit 2b at which each pear is transferred, in that the electronic unit is capable of choosing the exact moment at which to actuate the actuation element in order to make at least the first tray 4a tip: as has been seen, the moment chosen is conveniently the moment corresponding to the occurrence of the desired (preset) condition of mutual alignment.

Such result is therefore obtained even given the irregularities and peculiarities in the shape of pears (as with any other fruit and vegetable product A), in that the electronic unit and the transfer means adopted make it possible in each instance to vary the portion at which to perform the transfer, as a function of the variable peculiarities of each product A and of its configuration.

During the conveying, in addition to checking for flaws and more generally checking the color and size category, the assembly 1 enables an efficacious weighing of each pear, thanks to the ability to control the positioning, at least on the second line 3b.

In practice it has been found that the handling assembly according to the disclosure fully achieves the set aim, in that the transfer means, distributed at least along one part of the first conveyance and/or control line, are actuated by the electronic management and control unit, only upon the occurrence of a predefined condition of mutual alignment between the fruit and vegetable product to be transferred, which is conveyed by the first containment unit, and a second containment unit, and this makes it possible to transfer fruit and vegetable products between two handling lines, while at the same time being able to control their positioning, at least downstream.

The disclosure, thus conceived, is susceptible of numerous modifications and variations. Moreover, all the details may be substituted by other, technically equivalent elements.

In the embodiments illustrated, individual characteristics shown in relation to specific examples may in reality be substituted with other, different characteristics, existing in other embodiments.

In practice, the materials employed, as well as the dimensions, may be any according to requirements and to the state of the art.

The disclosures in Italian Patent Application No. BO2015A000148 (102015902341042) from which this application claims priority are incorporated herein by reference.

The invention claimed is:

1. An assembly for handling fruit and vegetable products, the assembly comprises:
    first containment units for horticultural products that can move along a first conveyance and/or a first control line and
    second containment units for fruit and vegetable products that can move along a second conveyance and/or a second control line, which is laterally adjacent and proximate to said first line, and further comprising:
    a plurality of transfer means configured for transferring the horticultural products, said means being distributed at least along a part of said first line and being selectively actuatable by an electronic management and control unit, for the transfer of each product from a said first unit to a respective said second unit in a portion chosen from a plurality of different portions of said first line, upon the occurrence of a predefined condition of mutual alignment between the horticultural product to be transferred, which is conveyed by said first unit, and said second unit, further comprising
    an electronic control apparatus, provided with a first video camera that faces said first line, for checking the color, the size and/or the presence of surface and pulp flaws on said horticultural products, which are supported and conveyed by said first units in a first arrangement, and a second video camera that faces said second line, for checking the color, the size and/or the presence of surface and pulp flaws on said horticultural products, which are supported and conveyed by said second units in a second arrangement that is obtained automatically as a consequence of the transfer the products from said first line to said second line,
    wherein said control apparatus comprises an electronic viewer associated with said electronic unit and arranged along said first line, for the acquisition of the information related to the position assumed by each fruit and vegetable product in the respective said first unit, said electronic unit being provided with an algorithm for calculating a portion of said first line that corresponds to the occurrence of said predefined condition of mutual alignment, as a function of the shape and of the speeds of said first unit and of said second unit, and as a function of said position detected by said viewer, said predefined condition corresponding preferably to the alignment of the fruit and vegetable product to be transferred, which is conveyed by the respective said first unit, with the central portion of a respective said second unit.

2. The handling assembly according to claim 1, wherein each one of said second containment units is associated with a respective device for weighing the conveyed horticultural product.

3. The handling assembly according to claim 1, wherein each one of said first units is constituted substantially by a first tray, which can move along a first guiding track which substantially defines said first line and can rotate about a first main axis, which is substantially parallel to said first track, said means comprising elements for actuating the rotation of respective said first trays about said first main axis, for their partial tipping and the consequent transfer of the corresponding horticultural product toward a respective said second unit, after such tipping the horticultural product passing automatically from said first arrangement to said second arrangement.

4. The handling assembly according to claim 3, wherein each one of said second containment units is constituted substantially by a second tray, which can move along a second guiding track which substantially defines said second line and has a shape and dimensions that are optionally different from those of said first tray, each one of said second trays being able to rotate about a second main axis, which is substantially parallel to said first main axis and to said second track, for their partial tipping in the opposite direction with respect to the partial tipping of said first trays, at least during the transfer of the respective horticultural product.

5. An assembly for handling fruit and vegetable products, the assembly comprises:
    first containment units for horticultural products that can move along a first conveyance and/or a first control line and
    second containment units for fruit and vegetable products that can move along a second conveyance and/or a second control line, which is laterally adjacent and proximate to said first line, and further comprising
    a plurality of transfer means configured for transferring the horticultural products, said means being distributed at least along a part of said first line and being selectively actuatable by an electronic management and control unit, for the transfer of each product from a said first unit to a respective said second unit in a portion chosen from a plurality of different portions of said first line, upon the occurrence of a predefined condition of mutual alignment between the horticultural product to be transferred, which is conveyed by said first unit, and said second unit, further comprising
    an electronic control apparatus, provided with a first video camera that faces said first line, for checking the color, the size and/or the presence of surface and pulp flaws on said horticultural products, which are supported and conveyed by said first units in a first arrangement, and a second video camera that faces said second line, for checking the color, the size and/or the presence of surface and pulp flaws on said horticultural products, which are supported and conveyed by said second units in a second arrangement that is obtained automatically as a consequence of the transfer the products from said first line to said second line,
    wherein said transfer means comprise at least one first guiding plate, which faces in a parallel arrangement and is proximate to said first line on the opposite side with respect to said second line, at least along the lateral wall of said first plate that faces said first line there being a plurality of inclined lanes, a first shank of each one of said first trays being selectively engageable following the actuation of the corresponding said actuation element in each one of said lanes, for the rotation of the corresponding said first tray as a consequence of the sliding of said first shank along said lane.

6. The handling assembly according to claim 5, wherein each one of said actuation elements comprises at least one actuator, which is integral with the respective said first unit and usually faces said first shank, each one of said actuators being selectively actuatable by said electronic unit in order to force the engagement of said first shank in a corresponding said lane.

7. The handling assembly according to claim 5, further comprising a second guiding plate, which faces in a parallel arrangement and is proximate to said second line on the opposite side with respect to said first line and is arranged along the path of second shanks of each one of said second trays, for their rotation as a consequence of the sliding of said second shanks on a contoured run defined by the top of said second plate.

8. The handling assembly according to claim 7, wherein each one of said trays is rigidly supported by a support which is pivoted, about the respective said main axis, to a slider, which slides along the corresponding said track, each one of said shanks extending from the corresponding said support on the opposite side with respect to the corresponding said tray.

* * * * *